(12) United States Patent
Kharchenko et al.

(10) Patent No.: US 7,978,820 B2
(45) Date of Patent: Jul. 12, 2011

(54) X-RAY DIFFRACTION AND FLUORESCENCE

(75) Inventors: Alexander Kharchenko, Almelo (NL); Roger Meier, Almelo (NL); Walter van den Hoogenhof, Almelo (NL)

(73) Assignee: Panalytical B.V., Almelo (NL)

( * ) Notice: Subject to any disclaimer, the term of this patent is extended or adjusted under 35 U.S.C. 154(b) by 89 days.

(21) Appl. No.: 12/604,305

(22) Filed: Oct. 22, 2009

(65) Prior Publication Data

US 2011/0096898 A1    Apr. 28, 2011

(51) Int. Cl.
*G01N 23/20* (2006.01)
*G01N 23/223* (2006.01)

(52) U.S. Cl. ............................................. 378/70; 378/44

(58) Field of Classification Search .............. 378/70–73, 378/79, 42, 45, 46, 205
See application file for complete search history.

(56) References Cited

U.S. PATENT DOCUMENTS

| | | | | |
|---|---|---|---|---|
| 3,903,414 | A * | 9/1975 | Herbstein et al. | 378/46 |
| 5,739,542 | A * | 4/1998 | Sudo et al. | 250/483.1 |
| 6,577,705 | B1 * | 6/2003 | Chang et al. | 378/45 |
| 7,796,726 | B1 * | 9/2010 | Gendreau et al. | 378/46 |
| 7,885,383 | B1 * | 2/2011 | He | 378/73 |
| 2005/0018809 | A1 * | 1/2005 | Gibson et al. | 378/71 |
| 2009/0141861 | A1 * | 6/2009 | Gaved et al. | 378/70 |

* cited by examiner

*Primary Examiner* — Irakli Kiknadze
(74) *Attorney, Agent, or Firm* — Blakely, Sokoloff, Taylor & Zafman

(57) ABSTRACT

An instrument capable of both X-ray diffraction, XRD, and X-ray fluorescence measurements, XRF, arranges an X-ray source 10 creating an incident X-ray beam directed to a sample on a sample stage. An X-ray detection system is mounted at a fixed angle 2θ for high energy energy dispersive XRD For XRF, an X-ray detection system is used.

13 Claims, 2 Drawing Sheets

US 7,978,820 B2

X-RAY DIFFRACTION AND FLUORESCENCE

FIELD OF INVENTION

The invention relates to an apparatus for both energy dispersive X-ray diffraction and X-ray fluorescence, and methods of operating the apparatus.

RELATED ART

X-ray diffraction (XRD) and X-ray fluorescence (XRF) are two well known ways of probing the structure and the elementary composon of samples. Generally, instruments are designed to carry out either one or the other method.

However, in some applications, instruments have been proposed that carry out both X-ray diffraction and X-ray fluorescence.

For example, U.S. Pat. No. 5,745,543 proposes an instrument that aims to overcome problems of low X-ray power arriving at the XRF detector by using a line-focus source, which enables XRD measurements, a plane or cylindrical analysis crystal together with a position-sensitive detector in the fluorescence measurement section. Thus no collimating system, which reduces the intensity, is used.

Another proposal is made by WO2008/107108 which includes a useful discussion of the difficulties that may be experienced when trying to combine XRD and XRF. In particular, the discussion highlights the difficulty of arranging an X-ray detector so that it can be moved over a wide angle range for XRD as well as being close to the sample for XRF. The intensity/sensitivity of each technique is optimised using a specific source for each.

Accordingly, there remains a need for smaller equipment with all, some or none of the following characteristics, in particular being easier to use, usable both for XRD and XRF, and which may be incorporated, for example, in production lines, manufacturing plants, and research institutions such as universities without incurring complex sample handling of more conventional designs.

SUMMARY OF INVENTION

The inventors have realised that the use of energy dispersive XRD is uniquely suitable for combination with XRF, and hence in a combined instrument which carries out both XRD and XRF.

Preferably, the range of energies used include high energy X-rays above 10 keV and preferably above 20 keV. The use of high energy energy dispersive (HEED) XRD is especially suitable as it allows good particle statistics. This can be done by using the continuum radiation of an XRF tube for XRD, rather than the characteristic lines of such a tube used for XRF. The characteristic lines suitable for XRF may be in the range of just below 3 keV (enhancing low Z number elements) and around 20 keV (enhancing the mid range elements). Using L-lines of 2.6 keV (eg Rh L-line) for XRD results in very poor penetration depth and thus poor particle statistics. Using instead the continuum radiation of such tube for diffraction allows the measurement in a suitable range of energy depending on the matrix of the sample.

BRIEF DESCRIPTION OF DRAWINGS

For a better understanding of the invention, embodiments will now be described, purely by way of example, with reference to the accompanying drawings, in which.

DETAILED DESCRIPTION

Figure 1:
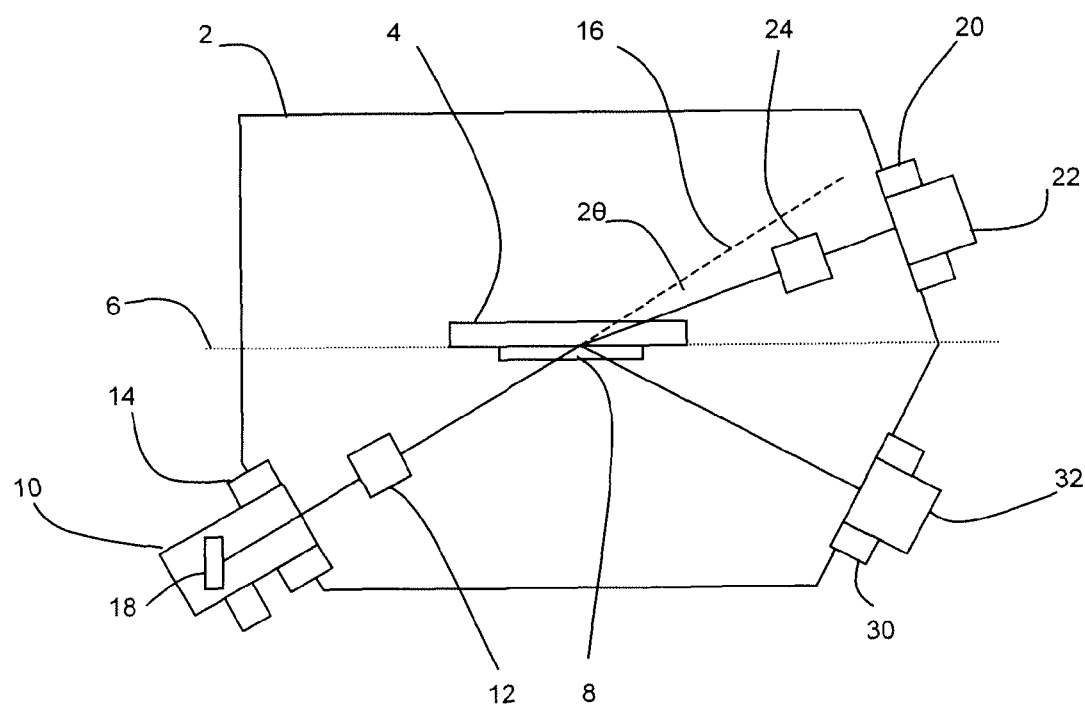
FIG. 1 illustrates apparatus according to the invention.

Referring to FIG. 1, apparatus according to the invention includes a housing 2 which may be evacuated or gas filled (He) in case of wet/liquid sample, and a sample holder 4 for mounting a sample. The sample holder may be adapted for holding a particular kind of sample, in the example cement. The sample holder 4 extends laterally in a direction that will be referred to as the sample plane 6 indicated by dotted lines.

An X-ray source 10 is provided on one side of the sample plane in line with a beam conditioner system 12 for collimating the X-rays to form an X-ray beam in incident X-ray direction 16. The X-ray source 10 is a source of both white X-rays, i.e. X-rays at a range of wavelengths, and characteristic lines. Further details will be discussed below. The X-ray source is mounted on an X-ray port 14 in the housing, which will be referred to as the X-ray source port 14 since it is for the purpose of mounting the X-ray source.

An X-ray port 20 is provided at a 2θ angle, in this example on the opposite side of the sample plane to the X-ray source for mounting an X-ray detection system 22. This X-ray detection system 22 is intended for energy dispersive X-ray diffraction measurement, so the X-ray port will be referred to as the XRD port 20 and the X-ray detection system as the XRD detection system 22. A beam conditioner system 24 to collimate the beams is provided in front of the XRD port 20 in order to get a beam to the XRD detection system 22.

In typical X-ray diffraction, the intensity of diffracted X-rays, which have the same energy as the incident X-rays, is measured as a function of angle 2θ to determine the structure of the sample. The relationship between the angle 2θ, the length scale d being probed and the wavelength λ is given by the well known Bragg equation nλ=2 d sin θ.

In contrast, in energy dispersive (ED) X-ray diffraction, a fixed angle 2θ is used, and the variable is energy. Using the relation between energy and wavelength λ=hc/E combined with Bragg law Energy dispersive diffraction can be done. Thus, instead of keeping the wavelength λ fixed and varying 2θ, the angle 2θ is fixed and the wavelength λ varied, by measuring at a number of energies. Accordingly, the XRD detection system 22 is an energy-dispersive detector in the most simple design.

This approach is very unusual indeed, especially in high accuracy applications, but has been proposed for the purpose of explosives detection by G. Harding, "X-ray scatter tomography for explosives detection", Radiation Physics and Chemistry volume 71 (2004) pages 869 to 881.

The inventors have realised that this very unusual approach to XRD is particularly suitable for combining with XRF applications.

A further port 30 is provided for mounting a further detection system 32, in this case for XRF, so the port will be referred to as XRF port 30 and the detection system 32 as XRF detection system 32. The port 30 is on the same side of the sample plane 6 as the source port 14. The XRF port can be chosen to be located for transmission or reflection. The use of transmission is useful for high atomic number elements.

However, for lower atomic number elements, the XRF port will be located on the same side of the sample plane 6 as the source port 14, as shown.

The XRF measurement will be explained in less detail than the XRD measurement, since the XRF measurement is relatively conventional. It is the ED XRD measurement that is highly unusual.

As will be appreciated from the above description, the source must be a source of X-rays at multiple energies. For the energy-dispersive XRD, "white" X-ray radiation is needed, i.e. X-ray radiation in a continuous spectrum, in contrast to typical tubes for XRD which may use highly monochromatic X-rays (for example from the characteristic lines), or a monochromator to produce such monochromatic X-rays. Thus, if only XRD is considered, the X-ray source 10 for energy dispersive XRD would preferably use a metal target for an electron beam where the metal target 18 is of a metal of a high atomic number for example as the intensity of the continuum increases with the atomic number of the target. Suitable targets include materials like Ta, W, . . . Au.

However, the requirements for XRF are different. For XRF, it is preferred to use a source with discrete lines, and typically a metal target 18 made of a material chosen to give characteristic lines to enhance low Z-elements as well as the mid range elements. Materials like Mo, Rh, . . . Ag give characteristic lines in the low energy range as well as in the range of 20 keV. As those materials have already a rather high atomic number they are also suitable to use their white radiation for ED XRD. Choosing the right $2\theta$ angle interference with the characteristic lines and diffraction lines can be avoided.

Thus, in the apparatus according to the embodiment, materials with atomic numbers from 42 to 46, such as Mo, Rh or Ag are particularly preferred.

Ultimately, an advantage of the invention is that it does not require a goniometer or moving parts, simply one X-ray source and two X-ray detectors mounted to ports in fixed locations. This results in an X-ray device capable of both XRD and XRF at modest cost.

The apparatus may be tailored to particular samples, especially in particular industries. For example, for the cement industry, the amount of free lime may need to be measured and this has a peak corresponding to a particular value of d. Thus, the exact fixed angle $2\theta$ in a given instrument will depend on the intended sample, and hence the value of d, but typical angles $2\theta$ in the range $5°$ to $12°$ or even $20°$ are generally preferred. Bragg's law $n\lambda = 2 d \sin \theta$ gives suitable values of $\theta$ and hence $2\theta$ when the energy range is known, and hence the range of energy (rather than wavelength $\lambda$) is also known.

For the measurement of pharmaceutical samples, however, the length scale d may be much larger and in this case $2\theta$ needs to be smaller. Accordingly, for the measurement of such samples, a range of angles $2\theta$ in the range $0.1°$ to $5°$ is preferred. Thus, overall, values of $2\theta$ may be from $0.1°$ to $20°$, and preferably in one of the narrower ranges $5°$ to $12°$ or $0.1°$ to $5°$, preferably $0.1°$ to $1°$, depending on the intended application.

In use, a sample is mounted on the sample stage, X-rays are directed onto the sample, and the X-ray spectra measured by both the XRD detection system 22 and the XRF detection system 32.

Figure 2:
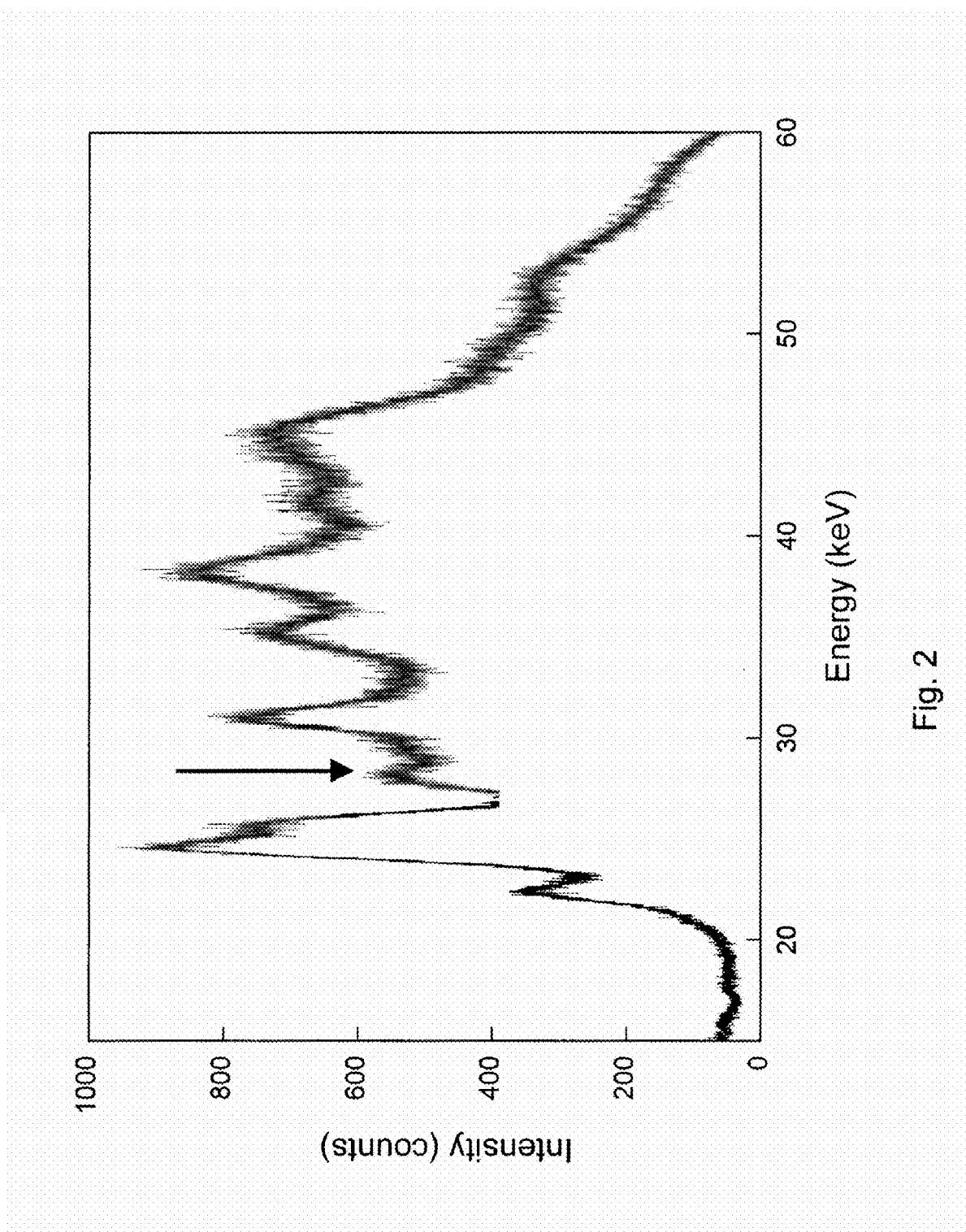
FIG. 2 illustrates results obtained on a cement sample.

In an example, a sample of cement was measured, the sample having a thickness between 3 mm and 4 mm. The angle $2\theta$ was $10.1°$ in the example. FIG. 2 illustrates the results from the XRD detector with various energies. The peak of most interest for testing cement is the free lime peak of d=0.245 nm, (thus at 28 keV with $2\theta$=10.1 degree), which is clearly visible and marked. It will be seen that good XRD results can be achieved even in this highly unusual configuration.

The detection systems may typically be energy dispersive systems as described above. In such approaches, the apparatus can have no moving parts, and in particular no goniometer.

However, in alternative embodiments the detection system may comprises a wavelength dispersive element, such as a crystal, a goniometer and a conventional X-ray detector. These may be combined in an integrated detection system that may be mounted on the appropriate port.

In an alternative, the goniometer may be omitted, and a single position insensitive detector used.

Another approach uses a position sensitive detector in combination with such a wavelength dispersive element, so that the detection system measures X-ray intensity as a function of energy using the combination.

The embodiment described above includes a single XRD port and a single XRF port. Note however that the housing may have further ports, to allow the XRD and XRF detection systems to be moved to different angles, or to allow multiple measurements simultaneously. In particular, there may be advantages in having multiple XRF detection systems to simultaneously measure XRF radiation at different energy ranges. In some cases, some of these XRF ports may be mounted on the opposite side of the sample plane to the X-ray source, i.e. on the same side as the XRD port.

Further, embodiments may have a pair of XRD ports, or more. For example, there may be one XRD port at an angle $2\theta$ in the range $5°$ to $12°$ and one in the range $0.1°$ to $5°$ for the different applications as described above.

Further, the embodiment above is described with the X-ray source and detection systems fixed on the ports. However, the instrument may in some cases be supplied with the source and detectors absent, with simply the bare ports.

The invention claimed is:

1. A combined X-ray diffraction, XRD, and X-ray fluorescence apparatus, XRF, comprising:
   an X-ray source which provides radiation simultaneously over a continuous range of wavelengths, the radiation including a plurality of characteristic lines;
   a beam conditioner system arranged to define an incident X-ray beam in the diffraction plane in an incident beam direction;
   a sample holder arranged to hold a sample in the incident X-ray beam, the sample holder defining a sample plane;
   an XRF port positioned for measuring X-rays off the sample with an X-ray detection system mounted on the port to do fluorescence analysis;
   an XRD port arranged at a fixed $2\theta$ angle to the incident beam direction for measuring diffracted X-rays, where $2\theta$ is in the range $0.1°$ to $20°$; and
   a beam conditioner system placed in alignment with the XRD port to select diffracted X-rays with an angle of $2\theta$ to the incident beam direction.

2. A combined X-ray diffraction and X-ray fluorescence apparatus according to claim 1, wherein the X-ray source is adapted to provide X-rays over a range of wavelengths being at least 10 keV wide and extending above 10 keV.

3. A combined X-ray diffraction and X-ray fluorescence apparatus according to claim 1, wherein the fixed angle $2\theta$ is in the range $5°$ to $12°$.

4. A combined X-ray diffraction and X-ray fluorescence apparatus according to claim 1, wherein the fixed angle $2\theta$ is in the range $0.1°$ to $5°$.

5. A combined X-ray diffraction and X-ray fluorescence apparatus according to claim 1 comprising an energy dispersive XRD detection system mounted on the XRD port, and an energy dispersive XRF detection system mounted on the XRF port.

6. A combined X-ray diffraction and X-ray fluorescence apparatus according to claim 5 wherein the XRD detection system comprises a goniometer, at least one crystal and at least one detector.

7. A combined X-ray diffraction and X-ray fluorescence apparatus according to claim 5, wherein XRD detection system comprises a wavelength dispersive element and a detector.

8. A combined X-ray diffraction and X-ray fluorescence apparatus according to claim 7, wherein the detector is a position-sensitive detector.

9. A combined X-ray diffract on and X-ray fluorescence apparatus according to claim 5, wherein the XRD detection system comprises an energy selective detector which is tunable to detect energies at a selected energy.

10. A combined X-ray diffraction and X-ray fluorescence apparatus according to claim 1 comprising a plurality of XRF ports.

11. A combined X-ray diffraction and X-ray fluorescence apparatus according to claim 1, comprising a plurality of XRD ports, wherein the XRF detection system comprises a goniometer, at least one crystal and at least one detector.

12. A combined X-ray diffraction and X-ray fluorescence apparatus according to claim 1, claim 2, claim 3, claim 4, claim 5, claim 6, claim 7, claim 8, claim 9, claim 10, or claim 11, comprising a plurality of XRD ports.

13. A method of operation of a combined X-ray diffraction and X-ray fluorescence apparatus comprising an X-ray source, a beam conditioner system, a sample holder, an X-ray fluorescence (XRF) port and an X-ray diffraction (XRD) port, the method comprising
    mounting a sample to the sample holder;
    providing radiation from the X-ray source simultaneously over a continuous range of wavelengths, the radiation including a plurality of characteristic lines;
    defining an incident X-ray beam incident on the sample in an incident beam direction in the diffraction plane;
    measuring X-rays at the XRF port for fluorescence analysis;
    selecting diffracted X-rays with a fixed angle of $2\theta$ to the incident beam direction; and
    measuring the intensity of selected diffracted X-rays as a function of energy.

\* \* \* \* \*

UNITED STATES PATENT AND TRADEMARK OFFICE
CERTIFICATE OF CORRECTION

PATENT NO. : 7,978,820 B2
APPLICATION NO. : 12/604305
DATED : July 12, 2011
INVENTOR(S) : Alexander Kharchenko, Roger Meier and Walter van den Hoogenhof It is certified that error appears in the above-identified patent and that said Letters Patent is hereby corrected as shown below:

In Column 5, Claim 9, line 1, delete "diffract on" and insert --diffraction--.

Signed and Sealed this
Thirteenth Day of March, 2012

David J. Kappos
*Director of the United States Patent and Trademark Office*

UNITED STATES PATENT AND TRADEMARK OFFICE
CERTIFICATE OF CORRECTION

PATENT NO. : 7,978,820 B2  Page 1 of 1
APPLICATION NO. : 12/604305
DATED : July 12, 2011
INVENTOR(S) : Alexander Kharchenko, Roger Meier and Walter van den Hoogenhof It is certified that error appears in the above-identified patent and that said Letters Patent is hereby corrected as shown below:

Column 5, line 14 (Claim 9, line 1) delete "diffract on" and insert --diffraction--.

This certificate supersedes the Certificate of Correction issued March 13, 2012.

Signed and Sealed this
Third Day of April, 2012

David J. Kappos
*Director of the United States Patent and Trademark Office*